United States Patent
Wilson

[11] Patent Number: 5,190,051
[45] Date of Patent: Mar. 2, 1993

[54] BRUXISM-RELAXING TRAINER

[76] Inventor: Mark J. Wilson, 23701 Mariner #212, Lniguel, Calif. 92677

[21] Appl. No.: 508,801
[22] Filed: Apr. 12, 1990
[51] Int. Cl.⁵ .............................................. A61B 5/103
[52] U.S. Cl. ........................................ 128/777; 433/6
[58] Field of Search ................... 433/6, 68, 27, 71, 72; 128/777, 776

[56] References Cited

U.S. PATENT DOCUMENTS

| | | | |
|---|---|---|---|
| 3,239,935 | 3/1966 | Shackelford | 433/27 |
| 3,349,489 | 10/1967 | Shackelford | 433/68 |
| 4,220,142 | 9/1980 | Rosen et al. | 128/777 |
| 4,255,138 | 3/1981 | Frohn | 433/6 |
| 4,521,186 | 6/1985 | Wodlinger et al. | 128/777 |
| 4,629,424 | 12/1986 | Lauks et al. | 433/6 |
| 4,838,283 | 6/1989 | Lee, Jr. | 128/777 |
| 4,842,519 | 6/1989 | Dworkin | 433/6 |
| 4,979,516 | 12/1990 | Abraham, II | 128/862 |

FOREIGN PATENT DOCUMENTS 0171960 11/1964 U.S.S.R. ............................. 128/777

Primary Examiner—Gene Mancene
Assistant Examiner—Adriene B. LePiane
Attorney, Agent, or Firm—Gilbert Kivenson

[57] ABSTRACT

A dental appliance for audibly signalling the onset of tooth clenching and thereby assist the wearer in altering the habit patterns which constitute bruxism. The appliance is self contained and does not require the use of external control boxes or telemetering equipment.

2 Claims, 2 Drawing Sheets

BRUXISM-RELAXING TRAINER

BACKGROUND AND OBJECTIVES OF THE INVENTION

The present invention relates to an intraoral alarm device which will signal the user whenever the teeth are clenched or ground during times when the jaw should be relaxed. Subconscious clenching and grinding (bruxism) occurs in many people as a result of nervousness both when awake and when sleeping. This results in undue wear of occluding surfaces, the onset of dental caries, muscular tension, headaches and other problems.

It is difficult to discontinue a subconscious practice because constant monitoring is required. If a signal or alarm can be provided to bring the practice to conscious attention, a habit of relaxing the jaw can be substituted.

Some equipment has in the past been devised to measure various occlusal forces, to study mastication, adjust dentures, trace hard-to-localize jaw pain, etc. Shackelford (U.S. Pat. Nos. 3,349,489 and 3,239,935) e.g. describes arcuate devices which are placed in the mouth to measure relative occlusal pressures. These devices contain pressure sensitive resistances which produce electrical signals and can actuate externally located metering devices. Connection from the resistors in the mouth to the metering devices is through multiconducting cable which exits through the lips and is coupled to an external control box. Lauks and Yankell (U.S. Pat. No. 4,629,424) by-pass the problem of the cable by employing a telemetry circuit installed in the removable mouthpiece along with pressure transducers. The telemetry circuit, which operates at radio frequencies, uses the pressure transducers to modulate the radio signal output. An external receiver demodulates the signal and displays it on a meter. Although an improvement over prior art, the system is complex, difficult to tune and requires an external control box.

In signalling the onset of bruxism it would be desirable to have a totally self-contained, intraoral appliance which can be worn during waking or sleeping hours without interfering with the normal activities or sleep of the individual. It is one objective of the present invention to incorporate pressure sensing means, a delay oscillator, a sound producing device and a power supply in a compact-enough form to fit into an introral appliance without causing user discomfort. It is a second objective to provide an appliance which the patient himself can readily insert, remove and keep clean during day or night use. It is a third objective to provide a device which will signal bruxism without disturbing others. These and other objectives will become apparent from the following description and the drawings.

SUMMARY OF THE INVENTION

The present invention is similar in external form to a tooth guard appliance used in many sports. A cross shelf holds electronic circuitry, a battery, an audio oscillator, a delay circuit and a miniature speaker. Several membrane switches are installed in the tooth contacting surface. With the appliance in place and one or more opposing teeth in contact, one or more of the switches connect the battery through the delay circuit to the oscillator. After a certain delay time, an audio tone is generated by the speaker. The tone can be heard by the user but is virtually inaudible to others. The sound warns him he is beginning to clench his teeth. If he is sleeping, the sound will awaken him. The discomfort will train him to relax his lower jaw.

All electrical components are imbedded in or coated with plastic to insulate them and to permit rinsing and cleaning of the appliance.

A second embodiment of the invention is designed for use on the lower teeth.

DESCRIPTION OF THE DRAWINGS

The invention will be described with reference to FIGS. 1, 2, 3, 4, 5 and 6.

DESCRIPTION OF THE INVENTION

Figure 1:
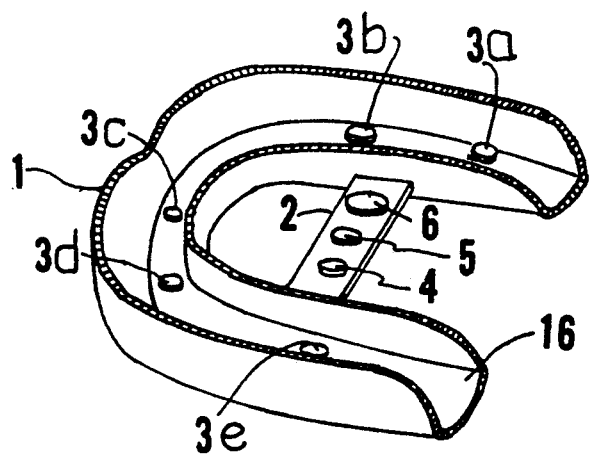
FIG. 1 is a perspective of the appliance showing the overall construction. The electronic components, the miniature speaker, the membrane switches, the battery, the delay circuit and the oscillator are pictured.

The first embodiment will be explained with reference to FIG. 1. A mouth guard construction 1 of a flexible material such as polypropylene, polyurethane or similar elastomer is employed as the base of the appliance. A cross shelf 2 serves to contain the electronic circuitry 5, the sound-producing means 6 and the battery 4. When positioned in the upper part of the mouth, the shelf 2 and its electrical apparatus can be adequately accommodated in the palatal space.

Figure 2:
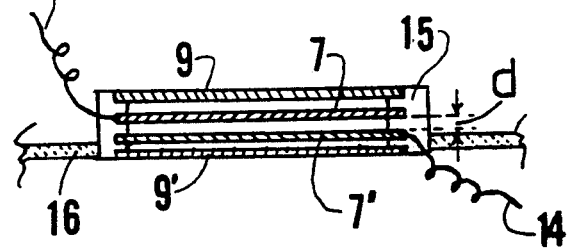
FIG. 2 is a cross section of a membrane switch in the open position.
Figure 3:
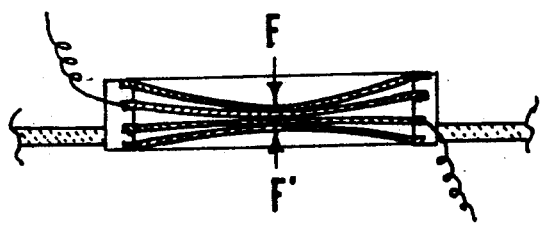
FIG. 3 is a cross section of the membrane switch of FIG. 2 in the closed position after being subjected to vertical forces.
Figure 4:
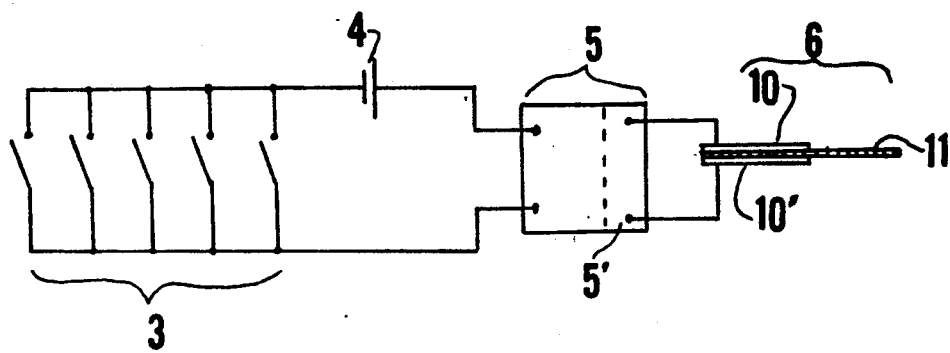
FIG. 4 is a schematic diagram of a suitable circuit for the invention illustrating the electrical connection of the various components.

Membrane switches 3a, 3b, 3c, 3d and 3e are distributed at various points along 16, the bottom surface of the appliance, and project through 16 so as to be able to be touched by the lower teeth. The construction of one of these switches is illustrated in FIG. 2. The flexible metal disks 7 and 7' are mounted in the plastic washer 15 with a vertical separation d of approximately 0.5 mm. The switch is sealed by flexible membranes 9 and 9'. Each switch is cemented into a circular opening in the bottom 16. Electrical wiring is imbedded in the walls of the appliance to shield it from exposure to mouth fluids. When occlusal forces F and F' (FIG. 3) are applied to the switch, metal disks 7 and 7' make contact. This connects the battery 4 to the timer-controlled audio oscillator to produce a delayed audible signal from the sound-producing means 6, FIG. 4.

Sound producing means 6 can be a speaker made up of the piezoelectric plastic film 11 and the electrodes 10 and 10'. A suitable film for this purpose is sold under the trade name "Kynar" and is available from the Pennwalt Corporation of Valley Forge, Pa. A speaker made in this way is of sufficiently small dimensions and low current requirement to be used in the present invention.

Figure 5:
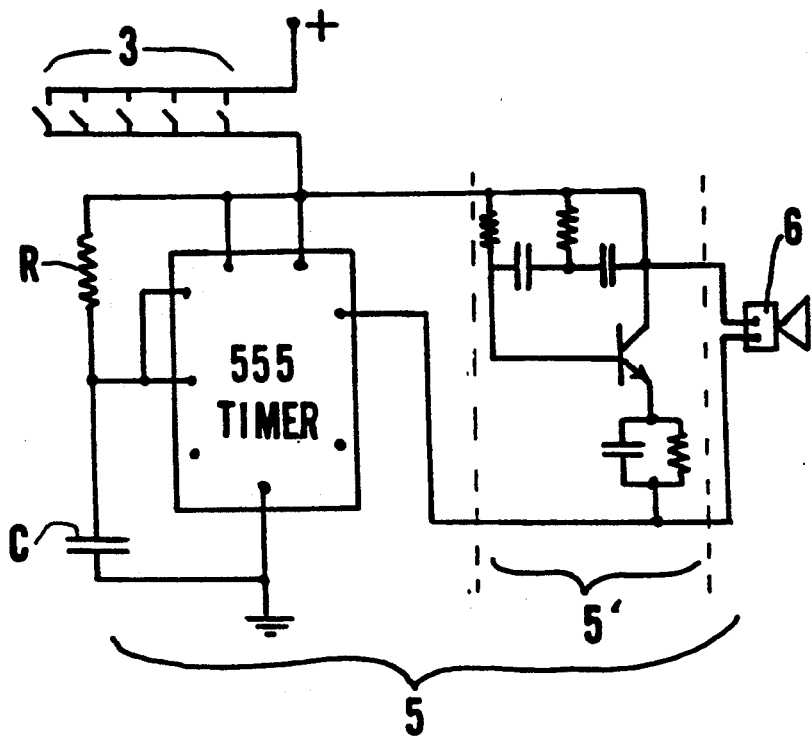
FIG. 5 is a schematic diagram of a delay circuit and oscillator for use with the invention.

A miniature timer-controlled audio oscillator is shown schematically in FIG. 5. When any of the switches is closed, voltage is applied to the 555 timer. After a preset interval (determined by the values chosen for R and C) the timer turns on the oscillator. This results in an audible alarm being generated in speaker 6. If tooth clenching is not continued for the preset time, there is no activation of the speaker. This prevents incidental contacts from producing frequent unnecessary alarms. It has been found that a delay of one to two seconds is effective in most cases but other delay times may be desirable with individual patients.

The circuit of FIG. 5 is only one of several which will serve this purpose and still be encompassed by the scope of this invention. Similarly alternative types of switches can be used to sense tooth contact.

Figure 6:
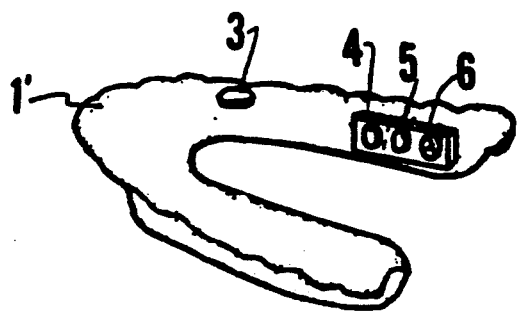
FIG. 6 is a perspective of a second embodiment of the invention suitable for use on the lower teeth.

A second embodiment of the invention is shown in FIG. 6. The mouth guard 1' is of an alternative design suitable for use on the lower teeth. The material of construction in this case is of a relatively rigid substance such as polyacrylate. The guard is shaped to fit against the lingual and upper surfaces of the lower teeth. The membrane switch 3 is cemented into a circular opening in the occlusal surface of the mouth guard. The delay oscillator 5, the speaker 6 and the battery 4 are mounted in a chamber formed in the inner surface of the mouth guard. Internal wiring is imbedded in the walls of the appliance. The single membrane switch used in this case is adjusted to close simultaneously with tooth contact at any point.

The amount of clenching force required to actuate the membrane switches in both embodiments may be varied by the choice of membrane thickness during switch construction and by variation in the separation (d in FIG. 2) between the metal disks 7 and 7'.

I claim:

1. A dental appliance to be worn over the upper teeth to signal when clenching occurs comprising:
   a. a flexible, tooth-conforming, U-shaped structure provided with a shelf bridging the arms of the U;
   b. pressure sensitive switches arranged in said structure so as to be actuated whenever extended contact occurs between the upper and lower teeth;
   c. a battery contained in said structure and fixed on said shelf;
   d. a delay circuit and oscillator mounted on the shelf of said structure;
   e. a sound producing means mounted on the shelf;
   f. wiring interconnecting the switches and battery with the delay circuit, the oscillator and the sound producing means;

whereby, with said appliance in place in the upper mouth, clenching of the teeth will close at least one of the switches and result, after a desired delay, in an audible signal in the mouth, said signal serving to call the attention of the user to the clenching and thus help eliminate habitual clenching.

2. A dental appliance to be worn over the lower teeth for signalling clenching comprised of:
   a. a rigid, U-shaped structure formed to fit over the lower teeth;
   b. a pressure sensitive switch arranged in said structure and adjusted to be actuated whenever clenching occurs between the upper and lower teeth;
   c. a battery, delay circuit, oscillator and speaker arranged inside said structure;
   d. wiring interconnecting the switch and battery with the delay circuit, the oscillator and the speaker;

whereby, with said appliance in place over the lower teeth, any clenching sustained longer than the delay will produce an audible signal to alert the wearer and help said wearer to form the habit of keeping his upper and lower teeth separated under normal conditions.

* * * * *